United States Patent
Montague et al.

(10) Patent No.: US 11,524,168 B2
(45) Date of Patent: Dec. 13, 2022

(54) SELF-CONTAINED, CONNECTED AUTOMATED EXTERNAL DEFIBRILLATOR SYSTEMS AND METHODS OF USE

(71) Applicant: HeartHero, Inc., Denver, CO (US)

(72) Inventors: Gary Montague, Denver, CO (US); Randolph Kerry Armstrong, Katy, TX (US); Satyajit Ketkar, Katy, TX (US)

(73) Assignee: HeartHero, Inc., Denver, CO (US)

(*) Notice: Subject to any disclaimer, the term of this patent is extended or adjusted under 35 U.S.C. 154(b) by 0 days.

(21) Appl. No.: 17/531,187

(22) Filed: Nov. 19, 2021

(65) Prior Publication Data

US 2022/0072322 A1   Mar. 10, 2022

Related U.S. Application Data

(63) Continuation-in-part of application No. 17/120,533, filed on Dec. 14, 2020, which is a
(Continued)

(51) Int. Cl.
*A61N 1/39*   (2006.01)

(52) U.S. Cl.
CPC ......... *A61N 1/3925* (2013.01); *A61N 1/3904* (2017.08); *A61N 1/3993* (2013.01)

(58) Field of Classification Search
CPC .. A61N 1/3925; A61N 1/3904; A61N 1/3993; A61N 1/08; A61N 1/37;
(Continued)

(56) References Cited

U.S. PATENT DOCUMENTS 5,713,925 A   2/1998 Sullivan et al.
5,817,151 A   10/1998 Olson et al.
(Continued)

FOREIGN PATENT DOCUMENTS

CN   101745180   6/2010
CN   105013085 A   11/2015
(Continued)

OTHER PUBLICATIONS

PCT Patent Application PCT/US2017/067442 International Search Report and Written Opinion dated Apr. 19, 2018.
(Continued)

*Primary Examiner* — Tammie K Marlen
(74) *Attorney, Agent, or Firm* — Avek IP, LLC (57) ABSTRACT

A self-contained automated external defibrillator (SCAED) system includes an AED operations block for controlling shock generation and administration, including pads for attachment to a patient, an electrocardiogram monitoring circuitry for monitoring patient heartbeat, shock generating electronics for generating electrical shock signal to be applied to the patient through the pads, a battery for supplying power to the AED operations block, a power management block for managing power consumption by the shock generating electronics and monitoring power status of the battery, a memory, a user-interface block for providing use instructions and receiving user input, and a controller for regulating the ECG monitoring circuitry, shock generating electronics, and the power management block. The SCAED system also includes a communications block for communicating with an external system separate from the SCAED system. The SCAED system further includes a security block for regulating data transfer between the AED operations block and the communications block.

8 Claims, 7 Drawing Sheets

Related U.S. Application Data continuation-in-part of application No. 15/847,826, filed on Dec. 19, 2017, now Pat. No. 11,103,718.

(60) Provisional application No. 62/947,959, filed on Dec. 13, 2019, provisional application No. 62/436,208, filed on Dec. 19, 2016.

(58) Field of Classification Search
CPC ............. A61N 1/3931; A61N 1/37252; A61N 1/37254; A61N 1/37258; A61N 1/3727
See application file for complete search history.

(56) References Cited

U.S. PATENT DOCUMENTS

| | | |
|---|---|---|
| 5,871,505 A | 2/1999 | Adams et al. |
| 5,908,443 A | 6/1999 | Brewer et al. |
| 6,353,758 B1 | 3/2002 | Gliner et al. |
| 6,456,877 B1 | 9/2002 | Fishler |
| 6,539,255 B1 | 3/2003 | Brewer et al. |
| 8,615,295 B2 | 12/2013 | Savage et al. |
| 9,026,147 B2 | 5/2015 | Galvin et al. |
| 10,029,109 B2 | 7/2018 | Beyer et al. |
| 10,071,256 B2 | 9/2018 | Montgomery et al. |
| 10,112,054 B2 | 10/2018 | Beyer et al. |
| D835,790 S | 12/2018 | Mercado et al. |
| D836,202 S | 12/2018 | Andrews et al. |
| 10,226,615 B2 | 3/2019 | Lang et al. |
| 10,449,380 B2 | 10/2019 | Andrews |
| 10,543,376 B2 | 1/2020 | Beyer et al. |
| 10,565,845 B1 | 2/2020 | Beyer et al. |
| 10,580,280 B1 | 3/2020 | Picco et al. |
| 10,621,846 B1 | 4/2020 | Beyer et al. |
| 10,665,078 B1 | 5/2020 | Picco et al. |
| D893,032 S | 8/2020 | Smith et al. |
| 10,737,105 B2 | 8/2020 | Andrew et al. |
| 10,773,091 B2 | 9/2020 | Andrews et al. |
| 10,799,709 B2 | 10/2020 | Teber et al. |
| 11,103,718 B2 | 8/2021 | Montague et al. |
| 2004/0015191 A1 | 1/2004 | Otman et al. |
| 2004/0143297 A1 | 7/2004 | Ramsey |
| 2004/0260376 A1 | 12/2004 | Craige et al. |
| 2005/0244709 A1 | 11/2005 | Bucher |
| 2007/0032830 A1 | 2/2007 | Bowers |
| 2007/0218869 A1 | 9/2007 | Thijs |
| 2007/0299473 A1 | 12/2007 | Matos |
| 2009/0005827 A1 | 1/2009 | Weintraub et al. |
| 2009/0240297 A1 | 9/2009 | Shavit et al. |
| 2009/0254136 A1 | 10/2009 | Powers |
| 2010/0070772 A1 | 3/2010 | Nakamura et al. |
| 2010/0241181 A1 | 9/2010 | Savage et al. |
| 2011/0071880 A1 | 3/2011 | Spector |
| 2011/0152702 A1 | 6/2011 | Goto |
| 2011/0190839 A1 | 8/2011 | Vaisnys et al. |
| 2011/0224745 A1 | 9/2011 | Magruder |
| 2012/0310315 A1 | 12/2012 | Savage et al. |
| 2013/0012151 A1 | 1/2013 | Hankins |
| 2013/0132465 A1 | 5/2013 | Brown |
| 2014/0004814 A1 | 1/2014 | Elghazzaw |
| 2014/0031885 A1 | 1/2014 | Elghazzawi et al. |
| 2014/0039593 A1 | 2/2014 | Savage et al. |
| 2014/0107718 A1 | 4/2014 | Foote et al. |
| 2014/0243914 A1 | 8/2014 | Freeman et al. |
| 2014/0277227 A1 | 9/2014 | Petersen et al. |
| 2014/0317914 A1 | 10/2014 | Shaker |
| 2016/0220833 A1 | 8/2016 | Qing et al. |
| 2016/0271408 A1 | 9/2016 | Newton et al. |
| 2017/0157415 A1 | 6/2017 | Horseman et al. |
| 2017/0325091 A1* | 11/2017 | Freeman ................ H04W 4/80 |
| 2018/0169426 A1 | 1/2018 | Montague |
| 2018/0161586 A1 | 6/2018 | Beyer et al. |
| 2018/0161587 A1 | 6/2018 | Beyer et al. |
| 2018/0161588 A1 | 6/2018 | Montgomery et al. |
| 2018/0161589 A1 | 6/2018 | Beyer et al. |
| 2018/0161591 A1 | 6/2018 | Andrews et al. |
| 2018/0243573 A1* | 8/2018 | Yoder ................ A61N 1/37252 |
| 2019/0044362 A1 | 2/2019 | Beyer et al. |
| 2019/0111272 A1 | 4/2019 | Hochhalter |
| 2019/0117983 A1 | 4/2019 | Andrews et al. |
| 2019/0117984 A1 | 4/2019 | Andrews et al. |
| 2019/0117987 A1 | 4/2019 | Beyer et al. |
| 2019/0117988 A1 | 4/2019 | Beyer et al. |
| 2019/0117989 A1 | 4/2019 | Andrews et al. |
| 2019/0143131 A1 | 5/2019 | Webster et al. |
| 2019/0329056 A1* | 10/2019 | Sjoquist ............. H04L 63/0823 |
| 2019/0329062 A1 | 10/2019 | Andrews et al. |
| 2019/0329257 A1 | 10/2019 | Teber et al. |
| 2019/0356492 A1* | 11/2019 | Picco .................... H04L 67/125 |
| 2020/0085333 A1 | 3/2020 | Freed et al. |
| 2020/0090483 A1 | 3/2020 | Picco et al. |
| 2020/0092700 A1 | 3/2020 | Picco et al. |
| 2020/0094038 A1 | 3/2020 | Andrews |
| 2020/0094039 A1 | 3/2020 | Andrews |
| 2020/0094044 A1 | 3/2020 | Andrews et al. |
| 2020/0108261 A1 | 4/2020 | Beyer et al. |
| 2020/0143651 A1 | 5/2020 | Beyer et al. |
| 2020/0152037 A1 | 5/2020 | Picco et al. |
| 2020/0215346 A1 | 7/2020 | Sturman et al. |
| 2020/0221263 A1 | 7/2020 | Sturman et al. |
| 2020/0242907 A1 | 7/2020 | Beyer et al. |
| 2020/0286352 A1 | 9/2020 | Beyer et al. |
| 2020/0286353 A1 | 9/2020 | Jafri et al. |
| 2020/0398066 A1 | 12/2020 | Teber et al. |
| 2021/0316152 A1 | 10/2021 | Sturman et al. |
| 2022/0072322 A1 | 3/2022 | Montague et al. |

FOREIGN PATENT DOCUMENTS

| | | |
|---|---|---|
| CN | 108671401 A | 10/2018 |
| CN | 111539866 A | 8/2020 |
| DE | 202004002106 U1 | 6/2004 |
| EP | 1157717 B1 | 1/2005 |
| EP | 2218478 A1 | 8/2010 |
| EP | 2450082 A1 | 5/2012 |
| EP | 3506981 A1 | 7/2019 |
| EP | 2879759 B1 | 10/2019 |
| EP | 3551285 A1 | 10/2019 |
| EP | 3681597 A1 | 7/2020 |
| JP | 2020503916 A | 2/2020 |
| JP | 2020524058 A | 8/2020 |
| KR | 102152282 A | 2/2016 |
| KR | 20160012239 A | 2/2016 |
| KR | 101780214 B1 | 10/2017 |
| WO | 2001010496 A2 | 2/2001 |
| WO | 2007069162 A1 | 6/2007 |
| WO | 2007135599 A2 | 11/2007 |
| WO | 2008057302 A2 | 5/2008 |
| WO | 2010066014 A2 | 6/2010 |
| WO | 2010146492 A1 | 12/2010 |
| WO | 2015143460 A1 | 10/2015 |
| WO | 2016092800 A1 | 6/2016 |
| WO | 2016149680 A1 | 9/2016 |
| WO | 2018111688 A1 | 6/2018 |
| WO | 2018232450 A1 | 12/2018 |
| WO | 2019070516 A1 | 4/2019 |
| WO | 2020055676 A1 | 3/2020 |
| WO | 2020056028 A1 | 3/2020 |
| WO | 2020068997 A1 | 4/2020 |
| WO | 2020142662 A1 | 7/2020 |

OTHER PUBLICATIONS

Automated External Defibrillators—New AEDs-AED.com, www.aed.com/new-aeds.html. Retrieved Sep. 14, 2018.

How Corpuls Works, Always Very Close to the User, https://corpuls.world/, Copyright 2017, Retrieved Sep. 14, 2018.

Heartsmart.com, Defibtech Lifeline AED, www.heartsmart.com/defibtech-lifeline-aed-defibrillator-p/dcf-100.htm, Copyright 2015, Retrieved Sep. 14, 2018.

Schiller The Art of Diagnostics, The World's First Pocket Defibrillator Fred Easyport, www.schiller.ch/ca/us/product/fred-easyport. Retrieved Sep. 14, 2018.

(56) References Cited

OTHER PUBLICATIONS

Phillips, Heartstart FRx Automated External Defibrillator, www.usa.philips.com/healthcare/product/HC861304/heartstart-frx-automated-external-defibrillator, Copyright 2004-2018, Retrieved Sep. 14, 2018.
Phillips, Heartstart OnSite AED, Product No. M5066A, www.usa.philips.com/healthcare/product/HCM5066A/heartstart-onsite-aed. Copyright 2004-2018, Retrieved Sep. 14, 2018.
Physio Control, Product Overview, www.physio-control.com/ProductsPrehospital.aspx, Copyright 2018, Retrieved Sep. 14, 2018.
Extended European search report (EESR) dated Jul. 10, 2020.
"AED Plus Technical Specifications", Dec. 31, 2011; Retrieved from the Internet: URL:https://web.archive.org/web/20120526132350if_/http://zoll.com/uploadedFiles/Public_Site/Products/AED_Plus/AED PlusSpecSheet.pdf; Retrieved on Jun. 30, 2020.
Okamura et al, "Evaluation of a Unique Defibrillation Unit with Dual-Vector Biphasic Waveform Capabilities: Towards a Miniaturized Defibrillator", Pace, Published Feb. 2017, pp. 108-114, vol. 40.
Dames, J.S., "Monophasic vs Biphasic Waveform Defibrillation," AED Superstore Website, published on Mar. 3, 2016 [online], retrieved from <URL:https://www.aedsuperstore.com/resources/monophasic-vs-biphasic/ [retrieved on Aug. 14, 2019], 9 pages.
Cahn, Michelle, "Connecting Your IoT Platform to 911: RapidSOS Emergency API," RapidSOS Website, published on Oct. 24, 2017 [online], retrieved from <URL:https://rapidsos.com/our-latest/product-spotlight-rapidsos-emergency-api/ [retrieved on Mar. 12, 2021], 3 pages.

\* cited by examiner

SELF-CONTAINED, CONNECTED AUTOMATED EXTERNAL DEFIBRILLATOR SYSTEMS AND METHODS OF USE

CROSS REFERENCE TO RELATED APPLICATIONS

This application is a continuation-in-part of U.S. patent application Ser. No. 17/120,533, filed Dec. 14, 2020, which claims priority to U.S. Provisional Patent Application No. 62/947,959, filed Dec. 13, 2019, and is a continuation-in-part of U.S. patent application Ser. No. 15/847,826, filed Dec. 19, 2017, now U.S. Pat. No. 11,103,718 issued Aug. 31, 2021, which claims priority to U.S. Provisional Patent Application No. 62/436,208, filed Dec. 19, 2016. Each one of these aforementioned applications is incorporated herein by reference in its entirety.

FIELD OF THE DISCLOSURE

Aspects of the present disclosure generally relate to automated external defibrillators (AEDs) and, more particularly, to compact AED systems suited for portable use.

BACKGROUND OF THE DISCLOSURE

According to the American Heart Association, there are approximately 424,000 Out of Hospital Cardiac Arrests (OHCA) that occur each year in the United States that are assessed by emergency medical personnel, and most of these cases are fatal. Studies have shown that communities with Automated External Defibrillator (AED) and cardiopulmonary resuscitation (CPR) training programs have achieved survival rates of 40% or higher for sudden cardiac arrest (SCA) sufferers. However, only a small percentage of OHCA will occur at a location at which an AED is available.

One approach to increasing the chance of survival for SCA sufferers is to make AEDs more readily available and accessible for more people. While there are initiatives to increase the dissemination of Public Access Defibrillators (PAD), research has also shown that 80% of OHCA happen in the home, where most people do not have access to an AED. The AEDs currently available on the market tend to be heavy, not portable, expensive, and intimidating to use for people without medical training. For example, U.S. Pat. Pub. No. US 2018/0169426, entitled "Automatic External Defibrillator Device and Methods of Use," which disclosure is incorporated herein in its entirety by reference, provides a possible solution to overcome the availability and accessibility problem by providing a compact AED device suitable for portability.

Figure 1:
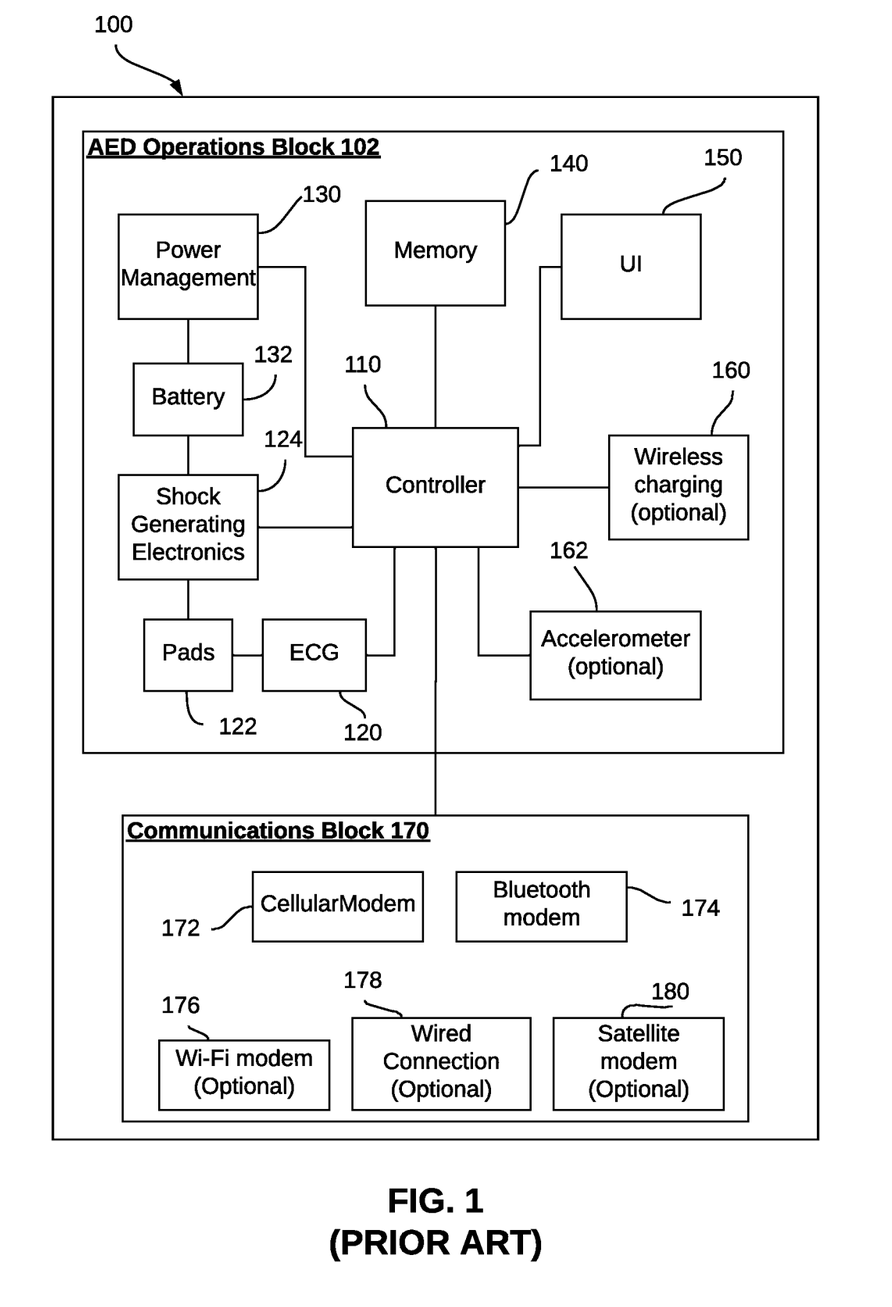
FIG. 1 illustrates a block diagram of a prior art AED, including an AED operations block and a communications block.

FIG. 1 illustrates a prior art AED including an AED operations block and a communication block, such as described in aforementioned U.S. Pat. Pub. No. US 2018/0169426. AED 100 includes features that allow AED 100 to connect with the outside world so as to provide additional functionality and allow use scenarios that have been heretofore impossible. An AED 100 includes an AED operations block 102, which includes various components that enable AED 100 to generate and deliver, within regulatory guidelines, an electric shock to a person in Sudden Cardiac Arrest. As shown in the embodiment illustrated in FIG. 1, AED operations block 102 includes a controller 110, which regulates a variety of components including an electrocardiogram (ECG) monitoring circuitry 120, which is in turn connected with pads 122. Pads 122 are configured for attachment to specific locations on the SCA patient for both obtaining ECG signals and administering the electric shock generated by shock generating electronics 124, which is also controlled by controller 110.

Additionally, AED operations block 102 includes a power management block 130, which is also controlled by controller 110 in an embodiment. Power management block 130 is configured for managing the power consumption by various components within AED operations block 102. For instance, power management block 130 monitors a charge status of a battery 132, which provides power to shock generating electronics 124. As such, controller 110 can alert the AED user if a low battery level is detected by power management block 130. Similarly, controller 110 can also regulate power management block 130 to control the on/off status of other components within AED 100 to minimize the power consumption by these other components while the AED is not being used. In an embodiment, for example, power management block 130 is configured to completely power down ECG monitoring circuitry 120 and shock generating electronics 124 when the AED is not being used.

Continuing to refer to FIG. 1, controller 110 is also connected with a memory 140, which stores information regarding AED 100, such as use history, battery status, shock administration and cardiopulmonary resuscitation (CPR) protocols, and other information used in the operation of AED 100.

Controller 110 further controls a user-interface (UI) block 150. UI block 150 includes, for example, voice and/or visual prompts for instructing the AED user on the use of AED 100 as delivered by, for instance, a haptic display such as a touch screen, light emitting diode (LED) indicators, liquid crystal display, speakers, switches, buttons, and other ways to display information to the user and/or for a user to control the AED. In an embodiment, UI block 150 can optionally include a microphone to receive voice inputs from the AED user. In an alternative embodiment, UI block 150 can optionally include an interface with an external application, such as a native or web app on a mobile device configured for communicating with AED 100. AED operations block 102 may optionally include wireless charging 160 and an accelerometer 162.

Still referring to FIG. 1, AED 100 includes a communications block 170, also controlled by controller 110. Communications block 170 provides connections to external systems and entities outside of the AED, such as emergency medical services, hospital emergency rooms, physicians, electronic health record systems, as well as other medical equipment, such as ventilators and an external ECG. In an embodiment, communications block 170 includes a cellular modem 172 and a Bluetooth modem 174. Optionally, communications block 170 also includes, for example, a Wi-Fi modem 176 for providing wireless connection to and from an external device, one or more wired connections 178 for providing direct wired connection to AED 100 such as via a local area network (LAN), cable, phone line, or optical fiber. Communications block 170 can also optionally include a satellite modem 180 for providing remote communications via satellite. The various communication modes within communications block 170 are configured to comply with regulatory guidance related to wireless technology, such as coexistence, security, and electromagnetic compatibility. By having a single controller (e.g., a microprocessor) control the various blocks within AED 100, the circuit design and firmware configuration of AED 100 is greatly consolidated over other AEDs with multiple processors, while enabling a reduction in power consumption of the device.

Figure 2:
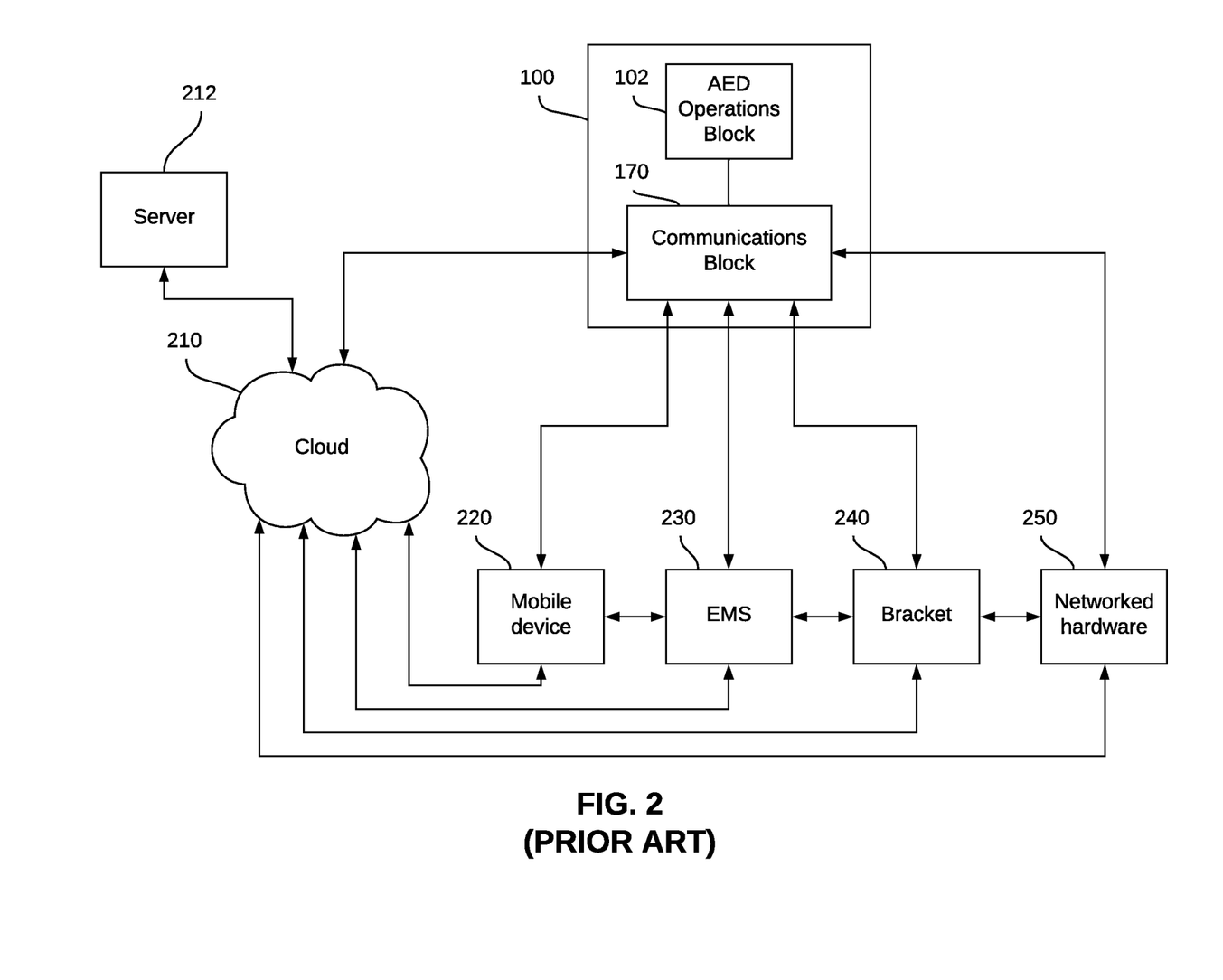
FIG. 2 shows a block diagram of communications interconnections enabled by the communications module of the prior art AED.

The combination of AED operations block 102 and communications block 170 enables a variety of new uses for exemplary AED 100. FIG. 2 shows a block diagram of communications interconnections enabled by communications block 170 of exemplary AED 100 shown in FIG. 1, in accordance with an embodiment. Communications block 170 provides communications capabilities to AED 100 so as to expand the usability of AED 100. In an embodiment illustrated in FIG. 2, communications block 170 is communicatively connected with cloud 210, which provides an internet-based communication platform. In the example shown in FIG. 2, cloud 210 provides a way for communications block 170 to communicate with a server 212 located, for instance, at the company that provides AED 100. Communication with cloud 210 can be performed, for instance, using cellular modem 172, Bluetooth modem 174, Wi-Fi modem 176, wired connection 178, and/or satellite modem 180 as described in reference to FIG. 1. Wired connection 178 includes, for instance, a cable line, a phone line, an optical fiber, and/or an electrical wire, where the wired connection forms, for example, a local area network.

Through cloud 210, server 212 may provide to communications module 170, and thus AED 100, a variety of data such as software and firmware updates, modifications to the shock administration and CPR guidance, device registration information, patient account information, presence of other nearby AEDs, and help files for error remediation if something is wrong with AED 100. Similarly, AED 100, through communications module 170, provides to server 212 additional information such as, for example, device registration status, battery status, device use history, device error log, and device location. It is noted, however, that interaction with server 212 is not required for AED 100 to communicate with other entities or to perform the operational tasks involved in the operation of AED 100 (e.g., activating the AED, monitoring the patient via AED operations block 102, generating and delivering electrical shock).

Continuing to refer to the embodiment illustrated in FIG. 2, communications module 170 is also configured to communicate with a mobile device 220 using, for example, cellular modem 172, Bluetooth modem 174, Wi-Fi modem 176, of satellite modem 180, as shown in FIG. 1. As an example, a native or web app is installed on mobile device 220 enables a user to perform AED-related tasks such as registration of the AED with the AED provider, and access to AED information and tutorials related to AED use. Optionally, mobile device 220 is connected to cloud 210 to be able to connect with server 212 therethrough, thus enabling the user to access data available at server 212. For instance, through an app installed on mobile device 220, a user can register an AED device, update personal account information, access training videos, verify the status and use history of an AED device, download treatment protocol and software updates, select language options, and/or locate nearby AED devices that have also been registered with server 212. Mobile device 220, through a native or web app installed thereon, can optionally be configured to contact emergency medical services (EMS) such as 911 dispatch, nearby hospitals, and physicians, as indicated by a box 230, automatically or when prompted by a user. Cloud storage can also be accessed to store AED usage and other information in virtual storage.

Other components can also be accessed by AED 100 through communications block 170. For instance, AED 100 can be mounted in a bracket 240 configured for providing additional or supplemental communications, power charging, and/or user interface functions to the AED. An example of such a bracket is disclosed in U.S. patent application Ser. No. 15/847,826 entitled "Automatic External Defibrillator Device and Methods of Use," filed on Dec. 19, 2017. Communication block 170 communicates directly with bracket 240 wirelessly or through a wired connection. Bracket 240 can in turn provide a communication link to, for instance, cloud 210, mobile device 220, EMS 230, and/or networked hardware 250, such as other AEDs, other external medical devices (e.g., pulse oximeter, ECG, CPR tracker), wearable devices (such as fitness trackers and heart monitoring consumer equipment, such as an Apple watch or a Whoop tracker) and a desktop or laptop computer. Networked hardware 250 can also be configured to directly communicate with AED 100 via communications block 170. As shown in FIG. 2, AED 100 may also directly access mobile device 220, EMS 230, bracket 240, networked hardware 230, and/or cloud 210 via communications block 170.

It should be noted that direct communications between AED 100 and EMS 230 may provide additional advantages. While AED 100 is a regulated device subject to regulatory approval by a governing body such as the Federal Drug Administration (FDA), any other peripheral device connected with AED 100 and essential for the operation of AED 100 as a life-saving device may also come under regulatory scrutiny. For example, if communications with EMS 230 is only allowed to go through, for example, cloud 210 and/or mobile device 220, then cloud 210 and/or mobile device 220 may also be subject to FDA approval as a medical device. Instead, by enabling direct communication between AED 100 with EMS 230, only components and software within AED 100 would be considered a standalone FDA regulated medical device, while cloud 210 and mobile device 220 would be considered peripheral data conduits only.

Having a variety of communications options, from cell modem, Bluetooth modem, Wi-Fi modem, wired connection, and satellite modem (optional) in a single AED allows a variety of communication modes such that, if the AED is placed in a location without one or more of the communication services, other communication modes can be used to ensure the connectivity of the AED. For instance, if AED 100 is placed is located where Wi-Fi is not available, it will likely be able to still send and receive information via one of the other communication modes, such as cell modem 172 or Bluetooth modem 174. Also, AED 100 may be configured for compatibility with Bluetooth- or radio frequency identification (RFID)- or near infrared (NIR)-based accessories, such as Tile Bluetooth trackers or the like, such that AED 100, through communications block 170, is able to communicate with other devices with such Bluetooth-based accessories. For instance, if several AEDs have been tagged with compatible Tile trackers, each AED 100 may be configured to enable "pinging" and locating other devices on a mesh network. Furthermore, AED 100 may be configured for compatibility with "smart home" applications such as Alexa or Nest. For instance, when AED 100 communicates with EMS 230 to direct emergency services personnel to a sudden cardiac arrest incident in progress, AED 100 can simultaneously communicate with the smart home application to ensure the house lights are on, doors are unlocked or garage doors are opened for EMS access, etc. Such tracker accessories and smart home applications may be implemented as part of networked hardware 250 in FIG. 2. As another embodiment, rather than relying on GPS satellite data for locating AED 100, cellular modem 172 may be used for providing location information of AED 100. For example, cellular modem 172 may include the necessary firmware and/or hardware for compatibility with a cellular-based locator service, such as those provided by Polte or Quectel, which allows for cellular triangulation of devices as well as z-axis (i.e., height/altitude) location.

SUMMARY OF THE DISCLOSURE

In accordance with the embodiments provided herein, there is provided a self-contained automated external defibrillator (SCAED) system. The SCAED system includes an AED operations block for controlling shock generation and administration, including pads for attachment to a patient, an electrocardiogram monitoring circuitry for monitoring patient heartbeat, shock generating electronics for generating electrical shock signal to be applied to the patient through the pads, a battery for supplying power to the AED operations block, a power management block for managing power consumption by the shock generating electronics and monitoring power status of the battery, a memory, a user-interface block for providing use instructions and receiving user input, and a controller for regulating the ECG monitoring circuitry, shock generating electronics, and the power management block. The SCAED system also includes a communications block for communicating with an external system separate from the SCAED system. The SCAED system further includes a security block for regulating data transfer between the AED operations block and the communications block.

In accordance with another embodiment, the communications block includes at least one of a cellular modem, a Bluetooth modem, a Wi-Fi modem, a wired connection, and a satellite modem. In a further embodiment, the communications block includes a communication processor configured for communicating with at least one of a mobile device, an emergency medical services system, a bracket configured for housing the SCAED system therein, a networked hardware, and cloud.

In accordance with a further embodiment, the security block includes a security processor configured for performing a security protocol on data transferred between the AED operations block and the communications block, the security protocol including at least one of: 1) validation of the data; and 2) authentication of a source of the data. Still further, the validation includes confirming integrity of the data received at the communications block prior to transmitting the data into the AED operations block. In another embodiment, the validation includes providing user output and receiving user confirmation on the data received at the communications block prior to transmitting the data into the AED operations block. In a further embodiment, the authentication includes confirming authenticity of the data received at the communications block prior to effecting any change to the SCAED system in response to the data. In another embodiment, confirming authenticity includes using at least one of a software key and a hardware key.

In accordance with a still further embodiment, a method for operating a self-contained automated external defibrillator (SCAED) system is disclosed. The SCAED system including an AED operations block for controlling electrical shock generation and administration and a communication block for communicating with an external system separate from the SCAED system. The method includes providing a security block for regulating data transfer between the AED operations block and the communication block, and upon receipt of data at the communication block, regulating transmission of the data to the AED operations block using the security block.

In another embodiment, regulating transmission of the data includes authenticating the data so received, validating the data so received, and transmitting the data to the AED operations block only if the data has been authenticated and validated.

In a further embodiment, authenticating includes at least one of using a software key, using a hardware key, and obtaining user confirmation. In a further embodiment, validating includes at least one of obtaining user confirmation and assessing integrity of the data.

DETAILED DESCRIPTION

The embodiments described in the present disclosure seeks to solve the problems described in the Background by providing an AED device with improved features over the existing products. It would be desirable to have a device that can significantly improve the outcome of an SCA patient by providing, even to a non-medically trained person, the ability to detect a shockable cardiac rhythm and apply a therapeutic electrical shock to the SCA patient. Therefore, there currently exists a need in the industry for a truly portable AED and associated methodology that closes the gap between time of incident, application of CPR, and delivery of shock. If more AEDs can be made available to more people, with portability, lower cost, and enhanced ease of use, then more lives can be saved in the event of an SCA occurring outside of a hospital setting. That is, like an EpiPen™ injector is prescribed for and carried by those diagnosed with potentially life-threatening allergies, a portable AED can be a necessary and routine item prescribed to those diagnosed as being at risk for SCA. A portable, affordable, and user-friendly AED with safe and simple application protocol is desired for such wide-spread proliferation of AEDs in the consumer market. Additionally, secure and streamlined connections to emergency personnel, external data sources, and peripheral devices would also be desirable.

A portable AED connected to the outside world via Bluetooth, WiFi, cellular, wired, or other connection mechanisms may provide new use scenarios and functionality unavailable to a disconnected AED. However, the connectivity comes with a price in that such connected devices can be at security risk.

For example, it may be possible for malicious parties to surreptitiously install malware on a connected AED from a remote location, thus compromising personal data stored on the AED. Similarly, the operation of the connected AED may be disrupted by an agent with malintent such that the connected AED malfunctions during use.

To address the aforementioned shortcomings of the existing art, certain embodiments of the system described herein provides a Self-Contained Automated External Defibrillator (SCAED) with security features to ensure secure transfer of sensitive data while protecting the SCAED from malicious cyber attacks. The shock generation and delivery operations of the SCAED are configured to be isolated from its communication functions such that the defibrillation functions of the SCAED are protected from outside access. The communication paths of the SCAED are protected by a security block providing onboard data risk mitigation at the SCAED, without relying on outside networks or servers. Essentially, the SCAED's AED functions are protected by security functions such that the AED is like a stand-alone AED device that will provide shock generation and delivery functions, independent of any external connections. Additionally, the security block protects and validates necessary data transfer, such as firmware updates, SCAED status alerts, and connections to outside networks, such as emergency response networks and connected medical equipment so as to provide the advantages of a connected AED albeit in a secure way.

Figure 3:
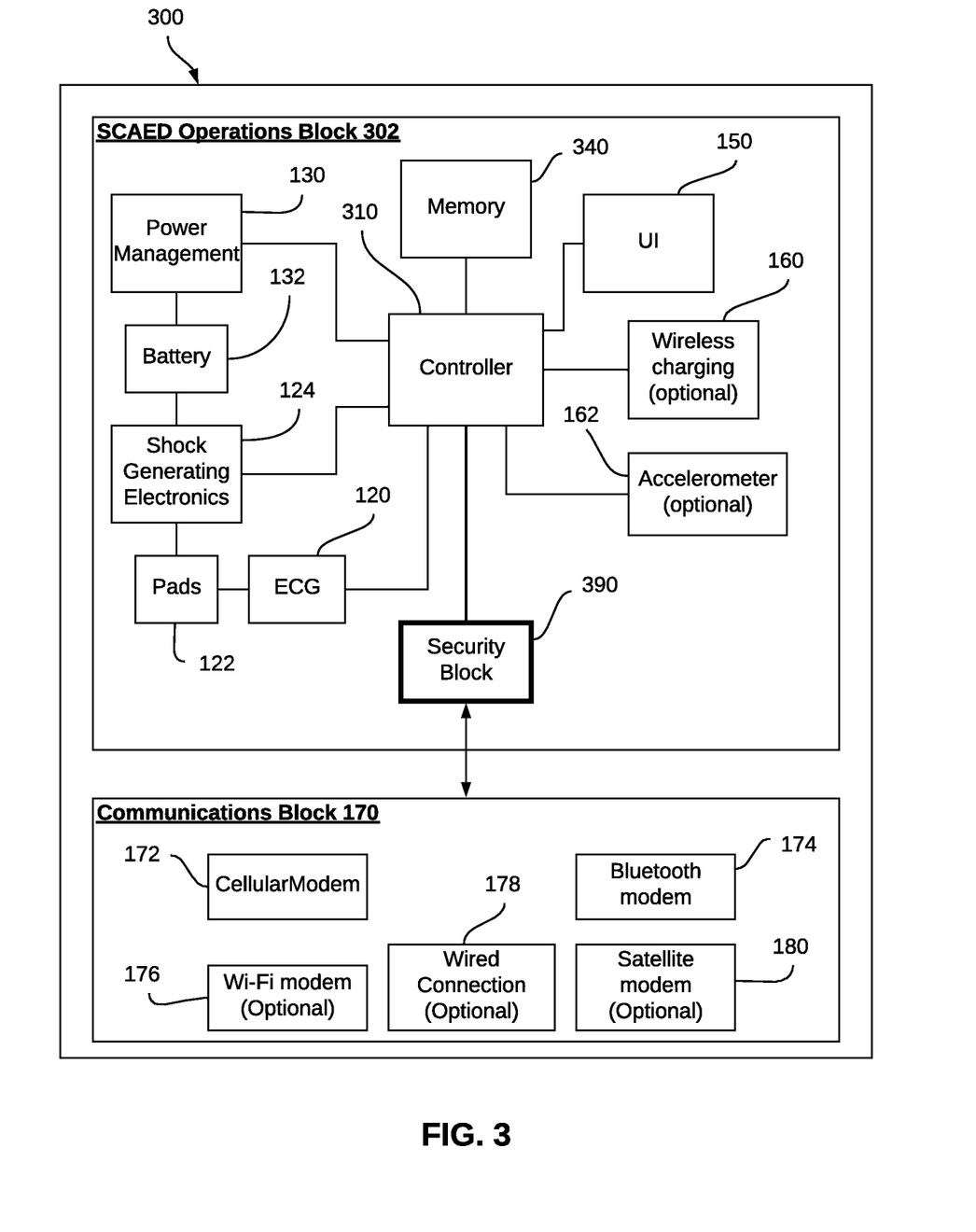
FIG. 3 illustrates a block diagram of an exemplary AED, including an AED operations block and a communications block interfaced through a security block, in accordance with an embodiment.

FIG. 3 illustrates a SCAED with security features, in accordance with an embodiment. In addition to the components of AED 100 of FIG. 1, a Self-Contained Automated External Defibrillator 300 includes a SCAED operations block 302 including a modified controller 310 and a modified memory 340, and integrated with a security block 390, which regulates the communications into and out of SCAED operations block 302.

Security block 390 includes security hardware and/or software to isolate modified controller 310, and thus the functions performed by SCAED operations block 302, from the outside world other than those communications validated and authorized by security block 390. In this way, security block 390 ensures SCAED operations block 302 is safely operable as an AED. That is, security block 390 isolates the rest of the components within SCAED operations block 302 to ensure independent and self-contained operations of the core AED components, namely modified controller 310, modified memory 340, ECG 120, pads 122, shock generating electronics 124, power management block 130, battery 132, and UI 150. Some examples of hardware and software suitable for implementation as part of security block 390 include encryption/decryption accelerators, request validation input/output or user interface devices, encryption/decryption algorithms, request validation algorithms, and operational sequences.

Modified controller 310 and modified memory 340 may be identical to controller 110 and memory 140 shown in FIG. 1, or be modified in order to better interface with security block 390. For example, controller 310 may be simplified to remove the functions and processing circuitry required in interfacing with communication block 170 such that the circuitry within controller 310 focus only on the AED operations. Modified memory 340 may include increased capacity with respect to memory 140 of FIG. 1 to accommodate the increased memory requirements of the processes implemented with security block 390 as described below. Alternatively, modified memory 340 may be identical to memory 140 of FIG. 1, and additional memory may be implemented aboard security block 390.

In an embodiment, security block 390 includes circuitry safety features to enable simplification of the electronics of the core AED components, thus further ensuring stable operations of the core AED components. Security block 390 includes hardware and/or software, such as memory and processing chips, to enable authentication, validation, and/or encryption of communications between SCAED operations block 302 and communications block 170, thus preventing malicious parties from accessing the core AED components.

As an example, any modification to the electric shock protocol or CPR instructions stored in memory 140 must be authenticated by security block 390. In another embodiment, while firmware updates are being made to the core AED components within SCAED operations block 302, security block 390 may store a copy of the existing firmware to enable restoration of the existing firmware if the update fails. Even before such updates are initialized within SCAED operations block 302, such modifications would require validation by security block 390 and only authenticated modifications would be allowed by security block 390. For instance, security block 390 may include hardware and/or software for authentication of communications purportedly received from the SCAED manufacturer or operator such that non-authenticated modifications to SCAED 300 is allowed.

In an embodiment, security block 390 is configured to periodically ping the SCAED manufacturer or operator entity server for device updates. That is, SCAED 300 pulls for device updates from an authenticated server, rather than having updates pushed directly to the SCAED. Then, once the presence of a necessary update is confirmed with the authenticated server, security block 390 obtains the update file and validates the file. If the update file does not contain the necessary data for validation, security block 390 does not allow the update file to be passed onto the core AED components. In other words, SCAED 300 itself authenticates and validates any changes to the device, rather than relying on an external source (e.g., the manufacturer or operator's network server) to push changes and updates to the SCAED operations. In another embodiment, if a user of SCAED requests a device update via UI 150 or an external app (e.g., a companion software application installed on a mobile device (not shown)), SCAED 300 will not install the update unless the update has been authenticated and validated by security block 390.

The integration of security block 390, while adding complexity to SCAED 300 over currently available AEDs, such as AED 100 of FIG. 1, provides several improvements over existing technologies. For example, as SCAED 300 is an independent, standalone device without reliance on an external network server or device to operate, SCAED 300 would be considered a whole medical device for purposes of regulatory approval by the US Food & Drug Administration (FDA). That is, if an app (or an external source like a network server) is remotely allowed to access the AED to make changes or updates thereto, this remote access capability would introduce a risk to the AED operations such that the FDA would require regulatory approval of the AED plus the app as a whole. In other words, an interaction with an external application or network server is not required for SCAED 300 to perform the operational tasks involved in the operation of SCAED 300 (e.g., activating the AED, monitoring the patient, generating and delivering electrical shock).

Further, whereas the additional computing resources within security block 390, such as memory and processing circuitry, adds computing resources not traditionally found in commercial AEDs, the security functions provided by security block 390 as well as the enabling of the simplification of the core AED components to focus solely on the effective and efficient operations of SCAED operations block 302 as a lifesaving AED provide advantages beyond those in currently available AEDs. In other words, the addition of security block 390 requires the inclusion of additional resources on SCAED 300, and the integration of memory and processing components within security block 390 and the programming of authentication and validation processes (e.g., handshaking protocols) require further sophistication and thoughtfulness in the design of SCAED 300 over existing AEDs. It is believed that the security advantages provided by the integration of the security block outweighs the disadvantages of the added complexity, especially in the recent sensitivity to cyber attacks and security breaches particularly for medical health-related and personal information that may be transmitted into and out of a connected AED.

Figure 4:
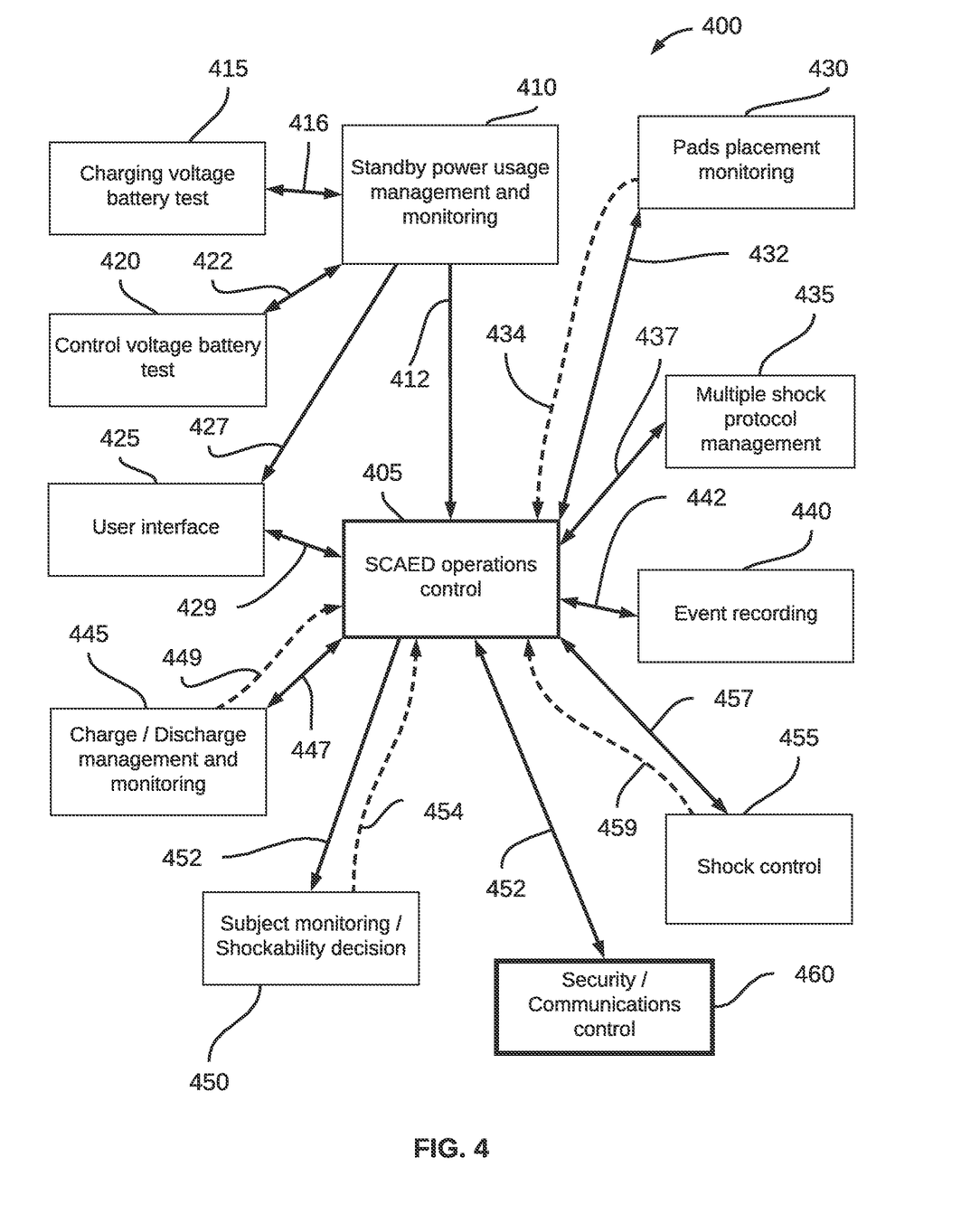
FIG. 4 shows a relational diagram showing the communications between an AED operations control module and other firmware within the AED module, in accordance with an embodiment.

Referring now to FIG. 4, a relational diagram 400 shows the communications between an AED operations control module 405 and other firmware within the AED operations block (e.g., SCAED operations block 302 of FIG. 3), in accordance with an embodiment. Most of the components shown in FIG. 4 has been discussed in the above mentioned U.S. patent application Ser. No. 15/847,826, with the addition of a security communications control block, as will be discussed directly hereinafter.

As shown in FIG. 4, an AED operations control module 405 includes circuitry and logic to orchestrate the overall operation of the AED module, such as AED module 100 of FIG. 1 and, more particularly, SCAED 300 of FIG. 3. AED operations control module 405 is in communications a standby power usage management and monitoring module (referred to as "Standby") 410, which manages the operations of the AED module when in standby mode. Standby 410 includes circuitry and logic to maintain, for example, a microprocessor and related circuitry in a low-power mode to facilitate a longer shelf life for the battery systems within the AED module. When the user activates the AED module for treatment use, standby 410 sends AED operations control module 405 a signal 412 to commence the treatment operation of the AED module.

In an embodiment, standby 410 communicates with a charging voltage battery test module 415, which includes circuitry and logic to test the battery capacity status of the battery, which powers the shock generation for the AED module. Periodically, standby 410 instructs charging voltage battery test module 415 to check the battery capacity of the main battery in the AED module, then send an indication via main battery status channel 416 back to standby 410.

In an exemplary embodiment, standby 410 is also connected with a control voltage battery test module 420, which tests a control battery for powering a microprocessor and related control circuits. Periodically, standby 410 instructs control voltage battery test module via a control battery status channel 422 to test the capacity of the control battery, then send an indication back to standby 410.

Additionally, in an embodiment, standby 410 communicates with a user interface (UI) module 425, which includes circuitry and logic to manage the conveyance of information to a user regarding device maintenance, as well as during AED operation. For instance, if either a signal from main battery status channel 416 or control battery status channel 422 indicates that the charge of the respective battery is low and requires replacement or maintenance, standby 410 sends a status alert signal 427 to UI module 425 to display an alert indication to notify a user of the problem. UI module 425 also is in direct communications with AED operations control module 405 via a user notification channel 429 to display user guidance or alerts during the operations of the AED module as necessary.

Continuing to refer to FIG. 4, in an exemplary embodiment, AED operations control module 405 is connected with a pads placement monitoring module 430, which includes circuitry and logic to monitor whether a user has properly attached a pair of cardiac pads onto the SCA patient. Upon initiation of the AED operations, and after AED operations control module 405 prompts the user to place the cardiac pads on the SCA patient via user notification channel 429 to UI 425, AED operations control module 405 checks with pads placement monitoring module 430 via a pads status channel 432 to ensure the cardiac pads have indeed been properly attached to the SCA patient. Additionally, pads placement monitoring module 430 can communicate with AED operations control module 405 on an asynchronous basis (indicated by a dashed arrow 434) to alert AED operations control module 405 in case, for example, if a cardiac pad becomes detached from the SCA patient. In an embodiment, the pads placement may be verified by measuring the impedance between the pair of cardiac pads or by other means, as known in the art.

Still referring to FIG. 4, AED operations control module 405 is also in communication with a multiple shock protocol management module 435 via a multi-shock channel 437, in an embodiment. Multiple shock protocol management module 435 includes logic to manage situational behavior of the AED in cases where the initial shock does not result in a return to normal sinus rhythm for the SCA patient. AED operations control module 405 also communicates with an event recording module 440 via an event recording channel 442. In an embodiment, event recording module 440 includes circuitry and logic to manage the capture of data related to, for instance, the condition of the SCA patient, therapeutic efforts by the AED, and external communications records.

In an exemplary embodiment, AED operations control module 405 manages a charge/discharge management and monitoring module 445. Charge/discharge management and monitoring module 445 includes circuitry and logic to manage the charging of the capacitor for storing the charge to a correct level to administer a therapeutic shock. Charge/discharge management and monitoring module 445 also includes circuitry and logic to manage the discharge of the capacitor if a therapeutic shock is not required, such that the AED can be handled safely and returned to storage in a safe state. Charge/discharge management and monitoring module 445 communicates with AED operations control module 405 via a charge management channel 447 to receive and acknowledge, for example, a charge or a discharge command. Also, charge/discharge management and monitoring module 445 can asynchronously communicate its status to AED operations control module 405 (as indicated by a dashed arrow 449), such as to indicate the capacitor charge has been reduced to a safe handling level sometime after a discharge command has been received from AED operations control module 405.

In an embodiment, AED operations control module 405 also controls a subject monitoring/shockability decision module 450. Subject monitoring/shockability decision module 450 includes circuitry and logic to manage the gathering of physiological measurements, such as cardiac rhythm, body impedance, and/or ECG signal. Subject monitoring/shockability decision module 450 also includes circuitry and logic to analyze the collected data to determine whether the SCA patient's condition is one that requires or can benefit from a defibrillating shock. AED operations control module 405 issues requests to Subject monitoring/shockability decision module 450 to determine shockability of the SCA patient via a subject monitoring channel 452. Whenever a determination of the shockability of the SCA patient has been made, sometime after receipt of the request for shockability determination from AED operations control module 405, subject monitoring/shockability decision module 450 sends an indicator back to AED operations control module 405 via an asynchronous communication (indicated by a dashed arrow 454). Finally, AED operations control module 405 also controls a shock control module 455 via a shock control channel 457. In an embodiment, shock control module 455 includes circuitry and logic to manage the determination of the shock waveform parameters, such as the durations of the positive and negative components to a biphasic shock, based on analysis of physiological measurements such as body impedance. Shock control module 455 further includes, in an embodiment, circuitry and logic to produce a biphasic shock waveform, according to the calculated parameters, then deliver the shock to the cardiac pads placed on the SCA patient. Shock control module 455 asynchronously sends a communication to AED operations control module 405 (indicated by a dashed arrow 459) to indicate, for example, that a shock has been delivered to the cardiac pads, as well as additional information such as the waveform parameters and patient vital signs.

Additionally, relational diagram 400 includes a security/communications control module 460. In an embodiment, security/communications control module 460 controls the functions of security block 390 of FIG. 3. For example, security/communications control module 460 validates and authenticates all outside communications requesting access to AED operations control module 405, as described above with respect to FIG. 3.

Figure 5:
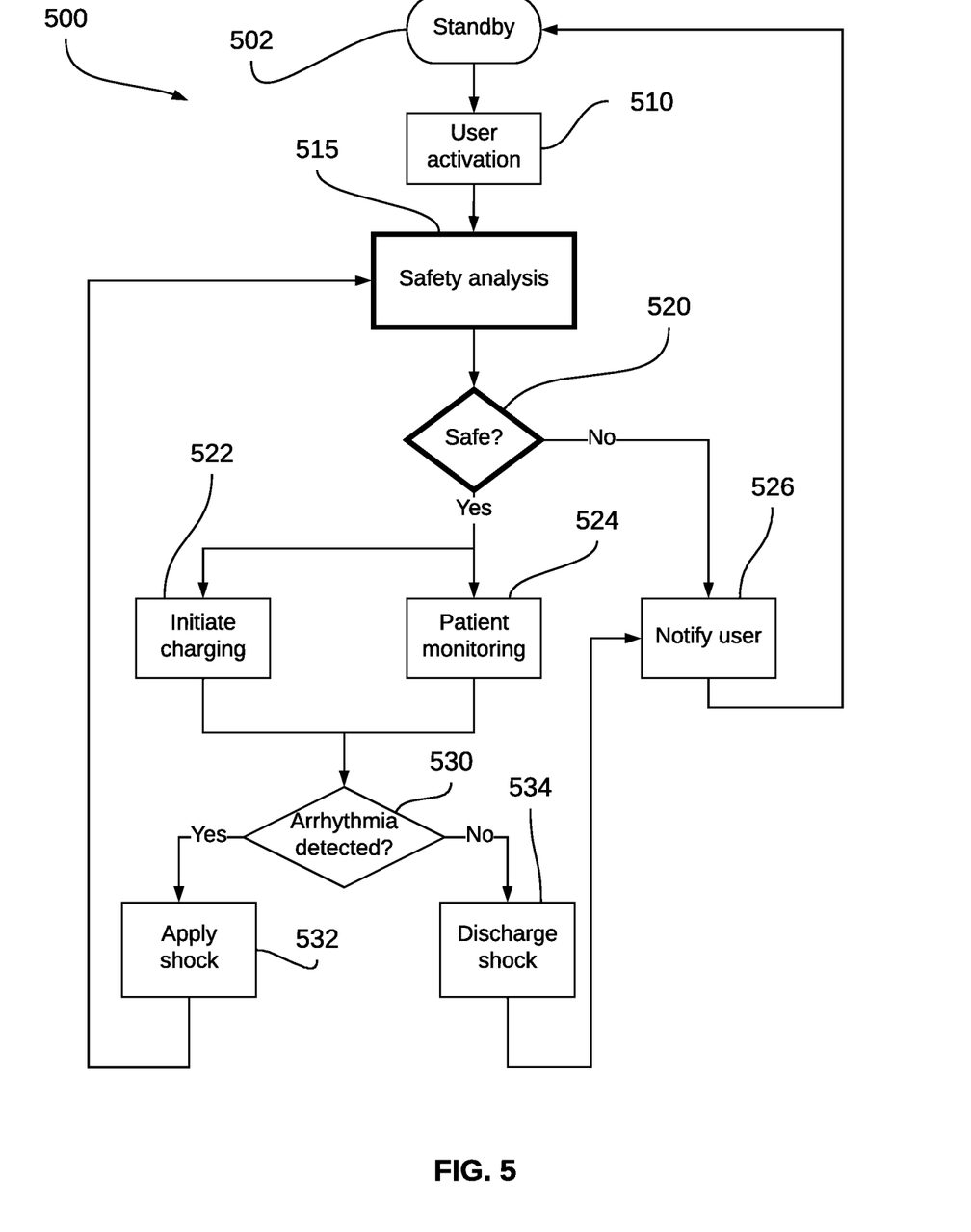
FIG. 5 shows a flow diagram illustrating an exemplary process flow for operating the exemplary AED, in accordance with an embodiment.

An example of a process enabled by SCAED 300 of FIG. 3 is illustrated in FIG. 5. FIG. 5 illustrates a process 500 where a safety validation of the AED is performed prior to the application of shock. As shown in FIG. 5, process 500 begins in a standby state 502. The SCAED is activated by a user in a step 510. For instance, the user may press an ON switch, or the SCAED may have sensed the cardiac pads connected with that SCAED has been released by the user. Process 500 then proceeds to a safety analysis step 515, in which protocols related to authentication and validation are activated. For instance, the SCAED may attempt to authenticate the user using mechanisms such as biometric identification (e.g., using a biometric sensor for capturing a biometric input such as an iris scan, fingerprint, or palm print), password entry, or other means. Alternatively, the validation may involve the sensing of an authorization key, such as a keychain tile or badge with an radio frequency identification (RFID) or near infrared (NIR) chip readable by the SCAED, which allows the user access to the shock generation and application functions of the SCAED. Alternatively, other factors that may affect the safe operation of the SCAED, such as the battery and/or circuitry status of the SCAED, proper attachment of the pads to the patient, environmental factors such as temperature and humidity, and timing of the most recent update, may be scanned for compliance with preset safety thresholds.

If a determination 520 determines that YES, it is safe to operate the SCAED, then the SCAED is instructed to initiate charging the shock generating electronics in a step 522, as well as to begin monitoring the patient in a step 524. If determination 520 is NO, it is not safe to operate the SCAED or the user is not authorized to use the SCAED, then the user is notified in a step 526 and process 500 returns to standby state 502.

After the charging circuitry has been activated in step 522 and patient monitoring has been initiated in step 524, the SCAED then performs the usual AED functions, such as determining whether shockable arrhythmia has been detected in a determination 530. If determination 532 finds YES, shockable arrhythmia has been detected, then process 500 proceeds to apply an electric shock to the patient in a step 532, and process 500 returns to safety analysis step 515. If determination 532 finds NO, shockable arrhythmia has not been detected, then the electrical charge is discharged in a step 534, and the user is notified of the determination and, optionally, recommended next steps, and process 500 returns to standby state 502.

Figure 6:
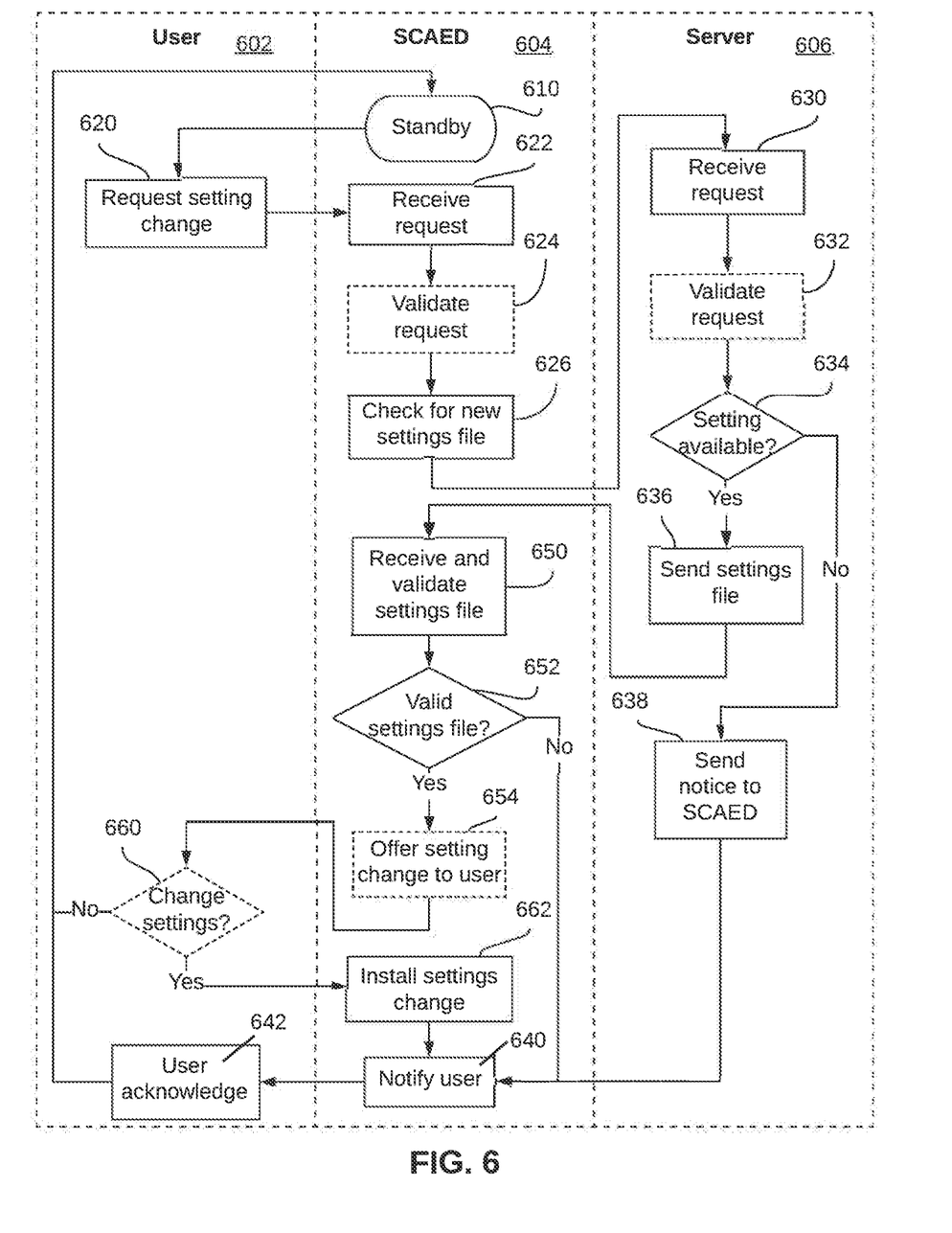
FIG. 6 shows a flow diagram illustrating an exemplary process flow for a user-initiated settings change, in accordance with an embodiment.

Another example use scenario is shown in FIG. 6, in which a process 600 for updating a setting in the SCAED is illustrated. Process 600 is divided into steps undertaken by a user (as indicated by a dashed box 602), the SCAED (as indicated by a dashed box 604), and a server belonging to the SCAED manufacturer or operator (as indicated by a dashed box 606).

Process 600 begins with the SCAED being in a standby status 610. Then the user requests a setting change in a step 620. A setting change may include, for example, a change in the language used by the user interface, firmware update, CPR guidance, shock generation and administration protocol, or any other setting affecting the operation of the SCAED. The user may provide the setting change request directly at the SCAED user interface, through an app on a mobile device, or through an AED network administration software, for example.

The SCAED receives the setting change request in a step 622. Optionally, such communication may be received by security block 390 of FIG. 3 such that the request itself may be authenticated and validated in a step 624. The SCAED then checks for the requested new settings file at the remote server (or optionally in a firmware library located on the SCAED itself) in a step 626. This communication with the remote server may also optionally take place through the security block on the SCAED to provide, for example, the necessary encryption or authentication keys to the remote server.

When the server receives the request for the settings file in a step 630, the server may optionally, in a step 632, authenticate and validate the request to ensure the request came from an authorized SCAED. Otherwise, a determination 634 is made to determine whether the requested setting file is available. If the requested settings file is available, then the server sends the requested settings file to the SCAED in a step 636. Step 636 may optionally include processes to incorporate authentication mechanisms into the settings file, such as encryption keys and authentication codes.

If the requested settings file is not available, then the server sends a notification to the SCAED in a step 638. The SCAED may notify the original user who requested the settings change in a step 640. Optionally, the user is required to acknowledge the notification in a step 642, and process 600 returns to standby status 610.

The settings file sent by the server in step 636 is received at the SCAED, the security block (e.g., security block 390 of FIG. 3) receives and validates the settings file in a step 650. A determination 652 is made whether the received settings file is an authentic, valid settings file. This determination may include steps such as file decryption using a preset key, looking for specific authorization codes, and other processes to ensure the received file is authentic prior to allowing the process to proceed.

If the received settings file is not determined to be authenticated, then process 600 proceeds to step 640 to notify the user, the user acknowledges the notification in optional step 642, and process 600 returns to standby status 610. If the settings file so received is determined to be valid, then optionally the SCAED performs a confirmation process with the user. As an example, the setting change is offered to the user in a step 654. The user is given an option 660 whether or not to perform the settings change. If the user chooses to change the settings, then process 600 proceeds to perform the settings change in a step 662. If the user chooses not to change the settings, then process 600 returns to standby status 610.

As mentioned above, the confirmation steps 654 and 660 are optional. For instance, for critical firmware updates, the SCAED may proceed directly from validation step 652 to settings change step 662 without user confirmation. As another example, if the settings change requires a change in the language used in the SCAED user interface, user confirmation in the new language may be included as a required step to ensure the SCAED user is indeed capable of interacting with the SCAED in the newly selected language. Otherwise, the SCAED may proceed directly to install the new settings file in step 662, without user confirmation.

Figure 7:
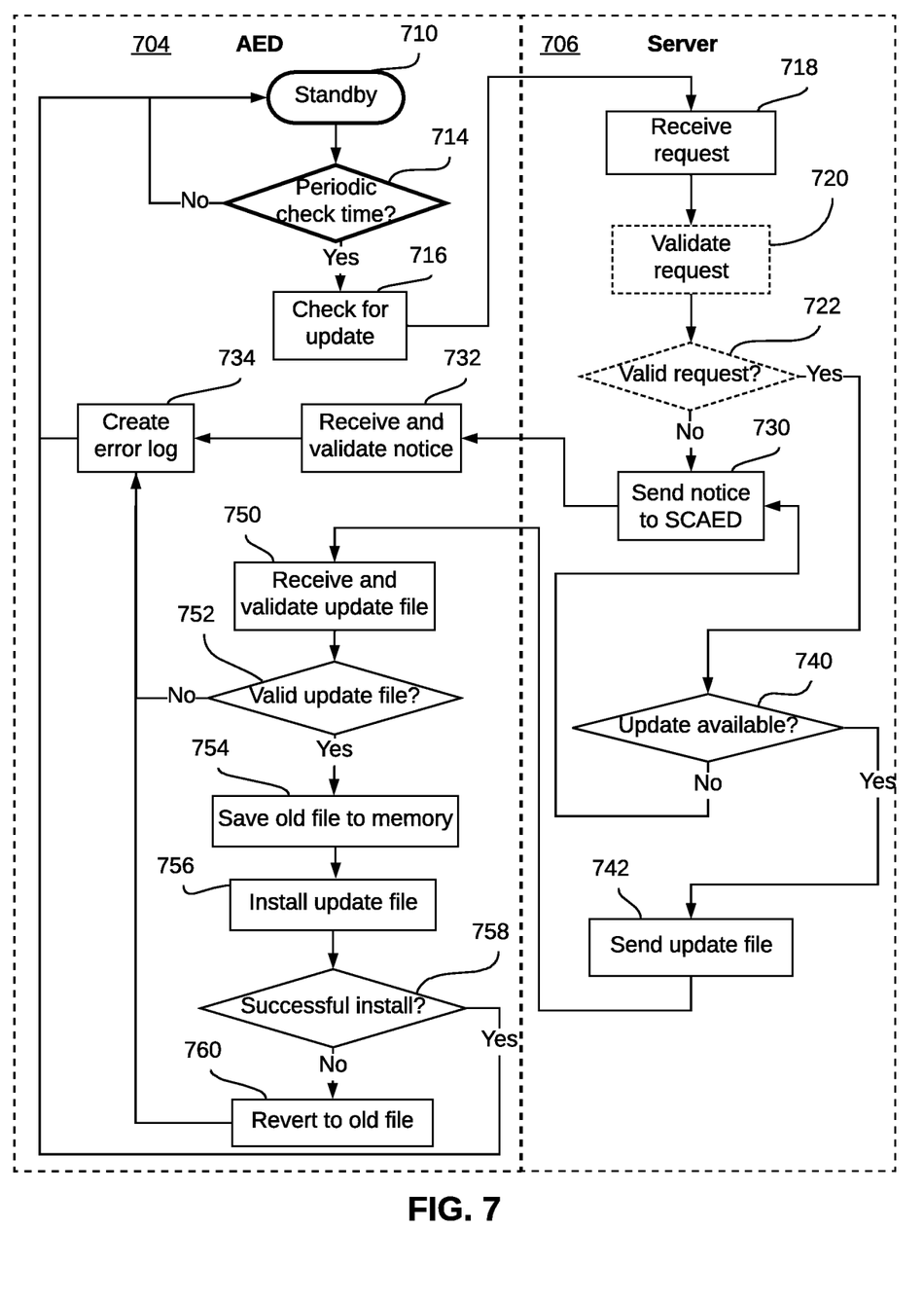
FIG. 7 shows a flow diagram illustrating an exemplary process flow for updating the exemplary AED, in accordance with an embodiment.

Another example of a process enabled by the inclusion of the security block within the SCAED is illustrated in FIG. 7. A process 700 may be used, for example, for installing firmware updates at the SCAED in a secure manner. As shown in FIG. 7, process 700 is divided into steps undertaken at the SCAED (indicated by a dashed box 704) and a server (indicated by a dashed box 706) such as a network server operated by a manufacturer or operator of the SCAED.

Process 700 begins with the SCAED in a standby status 710. In the illustrated example, the SCAED includes a timing mechanism (such as the combination of controller 310 and memory 340 in FIG. 3) to regulate a periodic check for firmware and/or software updates. A determination 704 is made to determine whether the timing mechanism has indicated it is time for a periodic check for updates. If the answer to determination 714 is NO, it is not yet time for a periodic check, then process 700 simply returns to standby status 710. If determination 714 concludes that it is time for a periodic check for updates, then the SCAED sends a request to the server to check for available updates in a step 716. The update request is received at the server in a step 718.

Optionally, the server validates the request in a step 720 to determine whether the request received was sent by an authorized SCAED. In this optional scenario, a determination 722 is then made whether the received request is valid. If determination 722 determines the request received did not originate from an authorized SCAED, for example, then a notice is sent to the SCAED in a step 730. The notice from the server is received at the SCAED and the authenticity of the notice is validated in a step 732. An error log is created in a step 734, then process 700 returns to standby status 710. If determination 726 determines the notice is not from a valid source, then an error log is created in a step 728, and process 700 may return to standby status 710. Alternatively, once an error log has been created in step 734, process may again check for updates in step 716.

Returning to determination 722, if the update request received at the server is determined to be from an authorized SCAED, then process 700 proceeds to a determination 740 to determine whether the requested update is available. Alternatively, process 700 may proceed directly from step 718 to determination 730, bypassing validation step 720 and determination 722.

If determination 740 concludes no update is available, process 700 again proceeds to step 730 to send a notice to the SCAED from which the request was received. An error log is created in step 728, and process 700 may return to standby status 710 or again check for updates in step 716

If the outcome of determination 740 is that a firmware and/or software update is available, then the relevant update file is sent to the SCAED in a step 742. Optionally, the sending of the update file in step 742 may be logged at the server in a separate step (not shown).

The SCAED then receives and validates the update file in a step 750. In a determination 752, a decision is made whether the update file so received is a valid file from an authenticated source. If determination 752 concludes the received file is not a valid, authenticated file, then process 700 creates an error log in step 734, followed by either return to standby status 710 or to check for the update again in step 716.

If determination 752 concludes the update file is indeed a valid file from an authenticated source, process 700 proceeds to a step 754 to save the old file, to be replaced, to memory. For instance, the old file may be saved to memory 340 or to an internal memory within security block 390 in FIG. 3. The SCAED then installs the update file in a step 756.

A self-check to determine the success of the update installation is performed in a determination 758. If self-check 758 concludes the update installation was successful, then process 700 returns to standby status 710.

If self-check 758 determines the update was not installed successfully, then the update is removed and the system is reverted to the previous state by retrieving the old file from memory in a step 760. Process 700 then an error log is created in step 734 and process 700 returns to standby status 710. Optionally, error log step 734 may include a counter such that, once a certain number of errors have been logged, the SCAED sends a notice to the SCAED user or the server to indicate an error status in the updating process cycle (not shown).

Although a few exemplary embodiments have been described, those skilled in the art will readily appreciate that many modifications are possible in the exemplary embodiments without materially departing from the novel teachings and advantages of the embodiments described herein. For example, as a variation to the process shown in FIGS. 6 and 7, the server may initiate contact with the SCAED with a notification that a new setting or an update is available. The SCAED would still go through a validation process to ensure the notification is legitimate (e.g., steps 622 and 624 in FIG. 6 or step 732 in FIG. 7) and a secure install process to ensure any newly received settings or update file is legitimate (e.g., steps 650, 652, and 662 of FIG. 6 or steps 750, 752, 754, 756, 758, and 760 of FIG. 7). In this way, while the initiation of the settings change or update install is received from an external source, the control of the risk mitigation and device security remains with the SCAED.

The illustrations of arrangements described herein are intended to provide a general understanding of the structure of various embodiments, and they are not intended to serve as a complete description of all the elements and features of apparatus and systems that might make use of the structures described herein. Many other arrangements will be apparent to those of skill in the art upon reviewing the above description. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

In the foregoing specification, specific embodiments have been described. However, one of ordinary skill in the art appreciates that various modifications and changes can be made without departing from the scope of the described embodiments as set forth in the claims below. Accordingly, the specification and figures are to be regarded in an illustrative rather than a restrictive sense, and all such modifications are intended to be included within the scope of present teachings. The descriptive labels associated with the numerical references in the figures are intended to merely illustrate the embodiments, and are in no way intended to limit the described embodiments to the scope of the descriptive labels. The present systems, methods, means, and enablement are not limited to the particular systems, and methodologies described, as there can be multiple possible embodiments, which are not expressly illustrated in the present disclosures. It is also to be understood that the terminology used in the description is for the purpose of describing the particular versions or embodiments only, and is not intended to limit the scope of the present application.

Some embodiments, illustrating its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. The disclosed embodiments are merely exemplary.

Accordingly, many different embodiments stem from the above description and the drawings. It will be understood that it would be unduly repetitious and obfuscating to literally describe and illustrate every combination and subcombination of these embodiments. As such, the present specification, including the drawings, shall be construed to constitute a complete written description of all combinations and subcombinations of the embodiments described herein, and of the manner and process of making and using them, and shall support claims to any such combination or subcombination.

What is claimed is:

1. A method for operating a self-contained automated external defibrillator (SCAED) system, the SCAED system including an AED controller for controlling electrical shock generation and delivery, a communication module for communicating with an external system separate from the SCAED system, and a security control module for performing security operations to ensure safe external communication via the communication module, the method comprising:
    performing, via the security control module, a safety analysis prior to enabling electrical shock generation and delivery,
    regulating data transfer between the AED controller and the communication module via the security control module,
    receiving, via a user interface of the SCAED system, a request for a settings change,
    checking, via the security control module, for the presence of a new settings file from a remote server,
    receiving, via the security control module, the new settings file from the remote server if available,
    validating, via the security control module, the new settings file,
    upon validation, offering a settings change via the user interface of the SCAED system, and
    upon receiving an indication for the settings change, installing the settings change to the SCAED system.

2. The method of claim 1, wherein regulating data transfer includes:
    authenticating the data so received,
    validating the data so received,
    upon determining that the data are authenticated and validated, transmitting the data to the AED controller, and
    upon determining that the data are not authenticated or validated, providing a notification via the user interface.

3. The method of claim 2, wherein authenticating includes at least one of using a software key, using a hardware key, and obtaining user confirmation.

4. The method of claim 2, wherein validating includes at least one of obtaining user confirmation and assessing integrity of the data.

5. The method of claim 1, wherein performing a safety analysis includes authenticating a user of the SCAED system.

6. The method of claim 1, comprising:
    pinging, via the security control module, a server for device updates;
    obtaining an update file and validating the update file; and
    upon validating the update file, transmitting the update file to the AED controller for updating the SCAED system.

7. The method of claim 1, comprising storing, via the security control module, a copy of an existing firmware of the AED controller to enable restoration of the existing firmware if an update fails.

8. The method of claim 1, comprising:
    checking periodically, via the security control module, for the availability of a software update from a remote server;
    when the software update is available, receiving an update file via the security control module;
    validating, via the security control module, the update file;
    saving an old file to a memory of the SCAED system; and
    installing the update file.

* * * * *